United States Patent [19]

Foguet et al.

[11] Patent Number: 5,135,943
[45] Date of Patent: Aug. 4, 1992

[54] 1H-IMIDAZOLE DERIVATIVE COMPOUNDS AND PHARMACEUTICAL COMPOSITIONS CONTAINING THE SAME

[75] Inventors: Rafael Foguet; Marcial Moreno; Manuel Raga; Rosa M. Cuberes; Jose M. Castello; Jose A. Ortiz, all of Barcelona, Spain

[73] Assignee: Ferrer Internacional S.A., Barcelona, Spain

[21] Appl. No.: 649,764

[22] Filed: Feb. 1, 1991

Related U.S. Application Data

[63] Continuation-in-part of Ser. No. 451,823, Dec. 15, 1989, abandoned, which is a continuation-in-part of Ser. No. 366,756, Jun. 14, 1989, abandoned, which is a continuation of Ser. No. 694,645, Jan. 24, 1985, abandoned.

[30] Foreign Application Priority Data

Feb. 2, 1984 [ES] Spain .................. 529608
Jun. 1, 1984 [ES] Spain .................. 533353
Aug. 6, 1984 [ES] Spain .................. 535656

[51] Int. Cl.$^5$ .................. A61K 31/415; A61K 31/38; C07D 403/12
[52] U.S. Cl. .................. 514/397; 548/336
[58] Field of Search .................. 548/336; 514/397

[56] References Cited

U.S. PATENT DOCUMENTS

| | | |
|---|---|---|
| 4,272,545 | 6/1981 | Walker .................. 548/336 |
| 4,402,968 | 9/1983 | Martin .................. 548/336 |
| 4,410,539 | 10/1983 | Cross et al. .................. 548/336 |
| 4,463,011 | 7/1984 | Ogata et al. .................. 548/336 |
| 4,496,572 | 1/1985 | Cross et al. .................. 548/336 |
| 4,500,536 | 2/1985 | Yoshida et al. .................. 548/336 |

Primary Examiner—Johann Richter
Attorney, Agent, or Firm—Michael J. Striker

[57] ABSTRACT

The 1H-imidazole derivative compound of formula I:

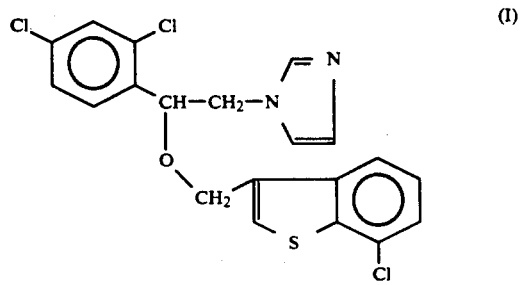

and its nontoxic addition salts, particularly the nitrate addition salt, are more effective as antimycotic agents and are unexpectedly safer than the corresponding prior art compounds, especially the compound in which the sulfur atom of the benzothiophene ring of the above compound is replaced by an oxygen atom. Pharmaceutical compositions containing an effective amount of the compound of formula I, e.g. 1 to 5% by weight, in a pharmaceutical carrier are safer, more effective, and, in some cases, more reliable with fewer side effects than currently used antimycotic preparations.

14 Claims, No Drawings

1H-IMIDAZOLE DERIVATIVE COMPOUNDS AND PHARMACEUTICAL COMPOSITIONS CONTAINING THE SAME

BACKGROUND OF THE INVENTION

This application is a continuation-in-part of application Ser. No. 451,823, filed Dec. 15, 1989, which is, in turn, a continuation-in-part application of Ser. No. 366,756, filed Jun. 14, 1989 and abandoned Apr. 5, 1990; which is a continuation of application Ser. No. 694,645, filed Jan. 24, 1985 and abandoned Jul. 27, 1989.

This invention relates to antimycotic pharmaceutical compositions and, more particularly, to 1H-imidazole derivative compounds and pharmaceutical compositions containing those compounds, especially antimycotic pharmaceutical compositions, i.e. pharmaceutical compositions for the treatment of infections in humans and animals, which are due to infection by fungi and yeast microorganisms. The invention also relates to fungicidal compositions for application to crops to destroy fungi and other microorganisms.

A number of compounds with antimycotic and/or fungicidal properties, which are useful in pharmaceutical compositions, are currently known. These include the commercially successful Miconazole having the formula II

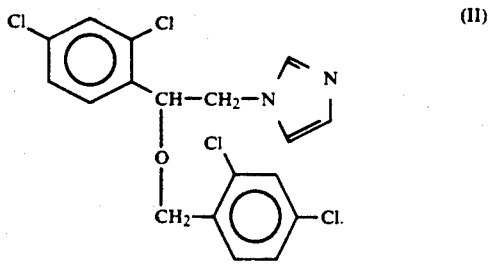

Miconazole has a structure chemically similar to the 1H-imidazole derivative compounds of the invention. Miconazole is effective against a number of yeasts, dermatophytes and fungi. This effectiveness can be measured by culturing these microorganisms in vitro and applying a preparation containing the antimycotic compound, Miconazole. The results of this type of *in vitro* experiment is expressed in terms of the Minimum Inhibitory Concentration (MIC), i.e. the minimum concentration which inhibits the growth of the microorganism. For example, the MIC for Miconazole against a particular *Candida albicans* strain is found to be 10.7 micrograms/milliliter. The effectiveness of Miconazole as an antimycotic compound is measured in vivo by applying a suspension containing the drug to the skin of a number of animals and measuring the proportion of animals on which growth of the microorganism is inhibited as a function of time. Typically, after 25 days, about ¼ of the animals were cured, when treated with a cream containing 2 % by weight Miconazole. Of course, any pharmaceutical preparation for treating a disease in a human must satisfy certain toxicity requirements. Therefore, toxicity tests are required to show that the preparation may be administered safely. Toxicity tests have been performed on the 1H-imidazole derivative compounds of the invention and on Miconazole and other known compounds having antimycotic properties. In toxicity tests the $LD_{50}$ (the dose at which 50 % mortality occurs) is measured. For Miconazole, for example, the $LD_{50}$ in mouse is about 2500 mg/kg for oral administration, 600 mg/kg for intraperitoneal administration and over 5000 mg/kg for subcutaneous administration.

Other compounds having a structure similar to applicants' compound include those described in U.S. Pat. No. 4,402,968, issued to Martin, Sep. 6, 1983. These compounds are also imidazole derivative compounds and have the following general formula III as claimed in the Martin Patent:

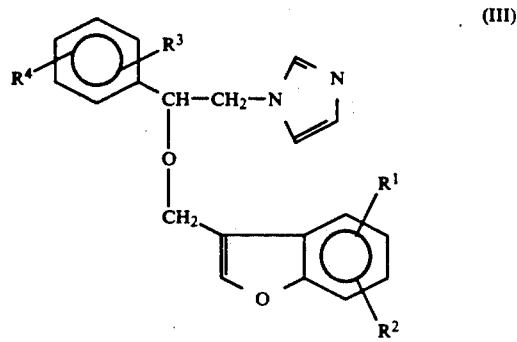

wherein $R^1$, $R^2$, $R^3$ and $R^4$ may be a hydrogen atom or a halogen atom, especially a chlorine atom. The in vitro fungicidal activity of one compound of formula III, in which all the R groups are chlorine radicals, was reported in the patent against several fungi. Measured in vitro against *Candida albicans* this compound has a MIC of about 10 micrograms per milliliter. A method of measurement of in vivo fungicidal activity was also described. However, as will be seen from the results described below, these compounds are comparatively toxic.

Other compounds having antimycotic properties are described in U.S. Pat. No. 4,272,545, issued to Walker. However, these antimycotic compounds have a structure which is considerably different from the structure of either the applicants or those of the Martin Patent. They have also been tested in vivo and in vitro and found effective against a large variety of fungi and yeast.

The current prior art antimycotic compounds, which are closest in structure to the applicants' compound, namely those of the Martin Patent, have an unexpectedly undesirably high toxicity, as measured in a variety of ways in comparison to the compounds described herein. Furthermore, the compounds of the present invention are more effective as in vitro fungicidal agents.

Other toxicological properties of the antimycotic compounds described in the Martin Patent are also poor. These poor toxicological properties imply that it is comparatively more dangerous to expose a human or pet to the compounds of the Martin Patent than to the compounds of the invention. The data, which will be presented below, also imply that 1H-imidazole derivative compounds of the invention can be applied in larger amounts, but as safely, as a correspondingly smaller concentration of the compounds of the Martin patent.

SUMMARY OF THE INVENTION

It is an object of the present invention to provide new 1H-imidazole derivative compounds having improved antimycotic and/or antifungicidal activity, but which are also unexpectedly safer, in comparison to the comparable prior art compounds.

It is another object of the present invention to provide new antimycotic IH-imidazole derivative compounds, which are more effective, are safer to use on humans and pets and also in larger amounts than the current comparable prior art compounds and which are more reliable and faster acting for some microorganism infections.

According to the invention, the 1H-imidazole derivative compounds having the above-mentioned improved pharmaceutical properties, including improved antimycotic activity and toxicological properties, comprise 1-[2-(7-chloro-3-benzo[b]thienyl)methoxy]-2-(2,4-dichlorophenyl)ethyl]-1H-imidazole, and nontoxic addition salts thereof, preferably the mononitrate and the heminaphthanlene-1,5-disulphonate.

The novel 1H-imidazole derivative compound of the invention also has the following general formula I:

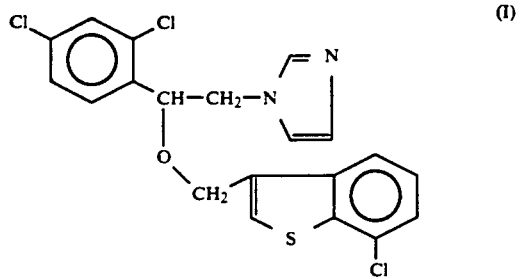

A number of other new 1H-imidazole derivative compounds of the following general formula I' have also been prepared and tested:

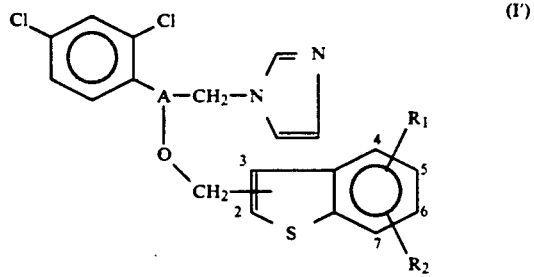

wherein A is an imino- , $$-\underset{|}{C}=N-, \text{ or a methyne}(-\underset{|}{C}H-)$$

group, $R_1$ and $R_2$ are independently hydrogen or halogen selected from chlorine, bromine or fluorine in any of the 2, 4, 5, 6 or 7 positions of the benzo[b]thiophene group, and the methylene -$CH_2$-group is bonded to the benzo[b]thiophene group in its 2 or 3 position. These compounds also show antimycotic properties.

The antimycotic compound of the invention, the compound of formula I, will be hence forth referred to as Sertaconazole, for convenience. Pharmaceutical preparations with antimycotic properties are described hereinbelow.

The compound of formula I had a melting point of 146-7° C. The corresponding nitrate addition salt had a melting point of 156-7° C. Mass spectra and elemental analysis also confirmed the structure of the compound of formula I. See Manuel Raga, Celia Palacin, Josep Ma. Castello and Jose Ortiz and Ma. Cuberes and Marcial Moreno-Manas, Eur. J.Med. Chem. 21, pp 329-332(1986).

PREPARATION OF THE DERIVATIVE COMPOUNDS

The compounds of the present invention may be prepared according to the following scheme:

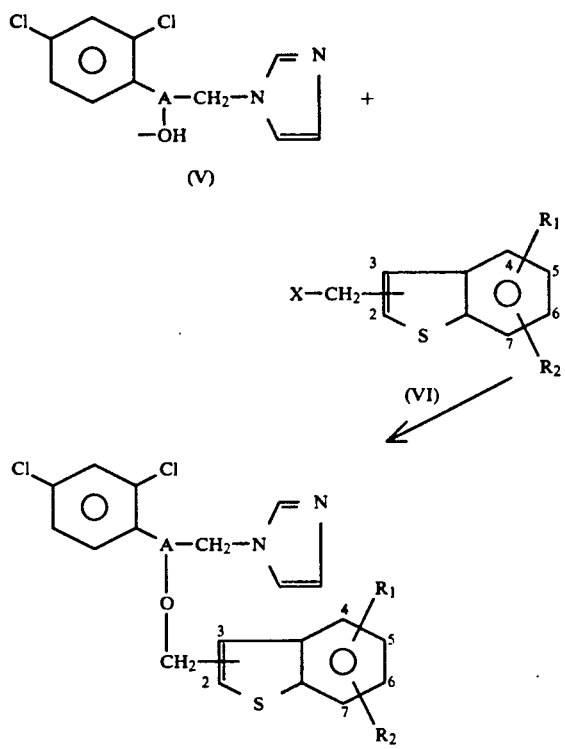

In the starting compounds of the formula V, A has the same meaning as stated above, and in the starting compounds of the formula VI, X is chlorine or bromine, $R_1$ and $R_2$ have the same meaning stated above and likewise, the methylene group (—$CH_2$—) is bonded to the benzo[b]thiophene group in the same position as defined above. A similar process is used to prepare the compounds described in the Martin reference referred to in the Background Section.

The reaction between the oxime or the alcohol of the formula V and the halides of the formula VI occurs conveniently in the presence of a suitable mineral base strong enough to ionize the compounds of the formula V such as hydroxides, or alkaline or alkaline-earth hydrides, with potassium hydroxide and sodium hydride, preferably employed.

The reaction is advantageously performed within a wide temperature range (from —55° C. to 100° C.) and in an aprotic solvent selected from an alkanone with up to 6 carbon atoms or a polyalkylated amide, with acetone or hexamethylphosphorotriamide preferably employed.

After purification, the acid addition salts may be obtained by treating with respective acids in a medium composed of an organic solvent. The organic solvent is an alcohol with 1 to 4 carbons, preferably ethanol or n-butanol, or may be a ketone such as acetone. A solvent which is a mixture of an organic solvent and water may also be used.

The described reaction steps lead to the compounds of the formula I according to the present invention.

The oxime and alcohol used as starting material of the formula V are already known and are obtained according to the processes described by Von. G. Mixich and K. Thiele (Arzneimittel-Forschung, 29(II), Nr.10, 1510-3, 1979)—oxime, .Z configuration—and by E.F. Godefroi, et al (J. Med. Chem., 12, 784-9, 1969)—Alcohol, for example by treating 1-(2,4-dichlorophenyl)-2-(1H-imidazol-1-yl) ethanone with hydroxylamine or sodium borohydride, respectively.

The halides of the formula VI are obtained by the known methods of organic chemistry, e.g.:

a) from benzo[b]thiophene either by chloromethylation (R. Neidlen and E.P. Mrugowski: Arch. Pharm. [Weinheim, Ger.,] 308(7), 513-9, 1975):

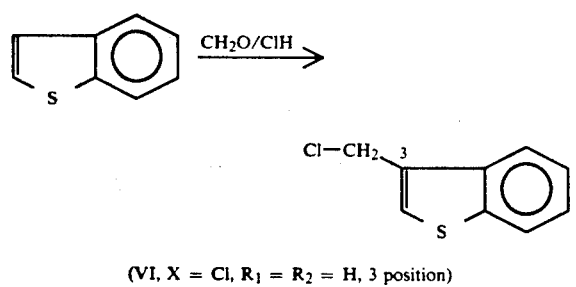

(VI, X = Cl, R₁ = R₂ = H, 3 position)

or by methylation and final bromination (D.A. Shirley and M.D. Cameron: JACS, 74, 664, 1952; U.S. Pat. No. 4,282,227):

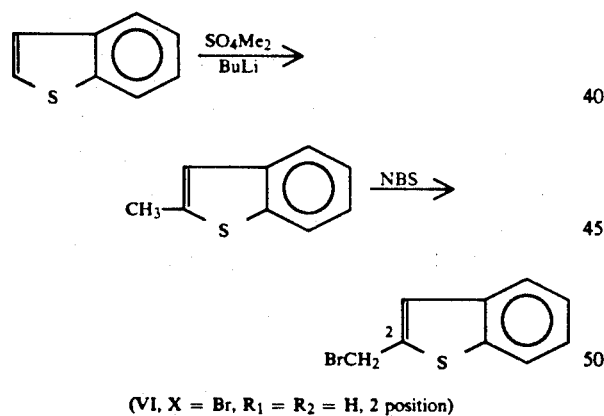

(VI, X = Br, R₁ = R₂ = H, 2 position)

b) from 2-chloro-3-methylbenzo[b]thiophene by bromination (European Pat. No. 54,233):

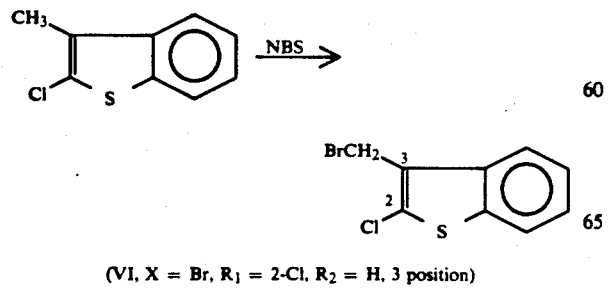

(VI, X = Br, R₁ = 2-Cl, R₂ = H, 3 position)

and 2-chloro-3-methylbenzo[b]thiophene is in turn obtained by chlorination of 3-methylbenzo[b]thiophene (V.I. Dronov et al, CA, 79, 115388f):

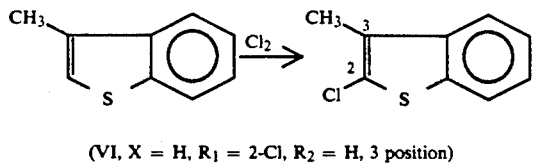

(VI, X = H, R₁ = 2-Cl, R₂ = H, 3 position)

c) from the corresponding thiophenol by total synthesis, for example, 2-chloro-2-propenyl-phenyl-thioether is formed by treating 2,3-dichloropropene, transposition in N,N-diethylaniline and cyclization with concentrated hydrochloric acid (W.K. Anderson and E.J. LaVoie, J. Chem. Soc., Chem. Commun., (5), 174, 1974; W.K. Anderson et al, J. Chem. Soc., Perkin Trans. 1, (1), 1-4, 1975):

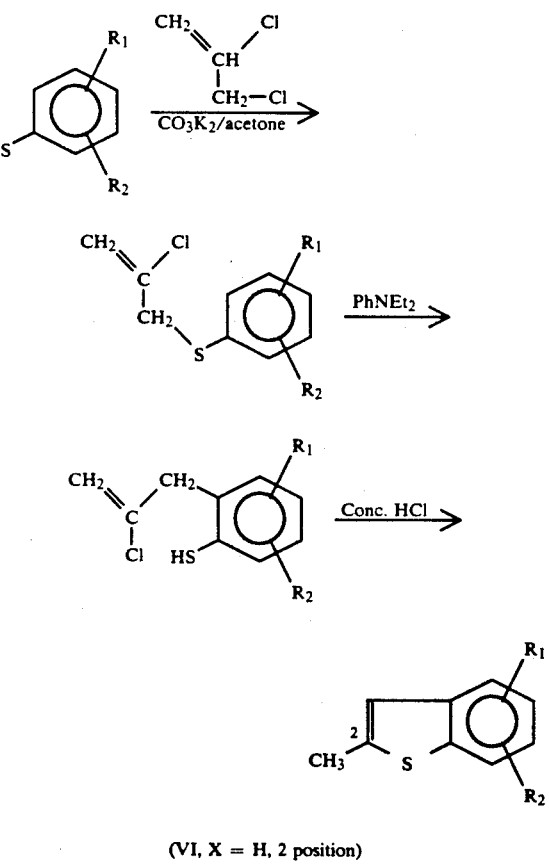

(VI, X = H, 2 position)

or by an alternative process also from the corresponding thiophenol by total synthesis, for example by forming respective 2-phenylthiopropionaldehyde acetal by treatment with 2-bromopropionaldehyde in sodium ethoxide and cyclization with an admixture of polyphosphoric acid and phosphorous pentoxide (Yasuo Matsuki and Fusaji Shoji, Nippon Kagaku Zasshi, 86,(10), 1067-72. 1965):

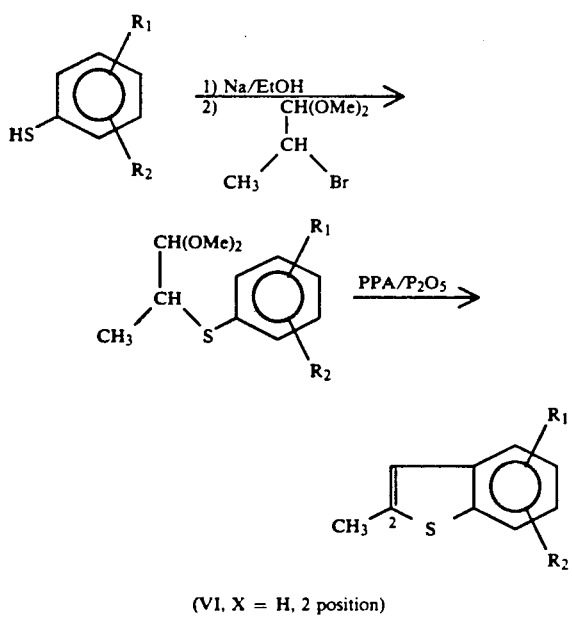

(VI, X = H, 2 position)

d) in a similar manner the 3-position compounds are also obtained from the corresponding thiophenol by total synthesis and forming respective phenylthioacetone by treatment with chloroacetone and cyclization with polyphosphoric acid (N.B. Chapman, et al, J. Chem. Soc. C., (5), pp. 512-22, 1968; N.B. Chapman, et al, ibid, (5), 2747-51, 1968):

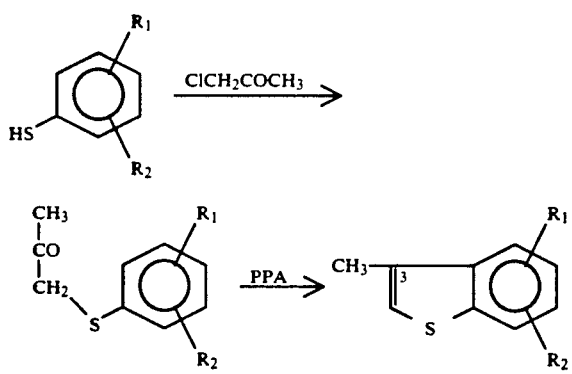

(VI, X = H, 3 position)
PPA: Polyphosphoric acid
NBS: N-bromosuccinimide

Halogenation of intermediates (VI, X=H) with N-bromosuccinimide or with N-chlorosuccinimide in carbon tetrachloride, under the conditions described by N.B. Chapman, et al; J. Chem. Soc. C., (5), 512-22, 1968) and N.B. Chapman, et al (ibid., (5), 2747-51, 1968), leads to the intermediates (VI, X=Br or Cl).

The starting thiophenol, when $R_1$ or $R_2$ are halogen in metaposition, leads to correspondingly substituted 4- or 6- position benzo[b]thiophenes, enabling the isomers to be separated by customary methods of organic chemistry. Column chromatography is a preferred method of separation.

COMPARATIVE STUDY OF PHARMACOLOGICAL PROPERTIES

Comparative in vitro and in vivo antimycotic activities of the compound of formula I, Sertaconazole, versus Miconazole and the compounds of the Martin patent, which have the closest structure to Sertaconazole, are reported hereinbelow. Clinical data are also included. The data show that Sertaconazole has a higher antimycotic activity than these prior art compounds. Furthermore, toxicological data for these compounds also shows that Sertaconazole is surprisingly and unexpectedly safer to administer to humans and pets in a method of treating an infection due to fungi or yeast.

The compounds of the Martin patent, which are the closest in structure to Sertaconazole, also have an unexpectedly large toxicity and are much less safe than Miconazole. In view of this finding, it is not surprising that Miconazole is the more frequently used compound commercially. As a result, comparison has been made with Miconazole as well as with the compounds described in the Martin patent.

1. In vitro Fungicidal Activity Measurements

Minimum Inhibitory Concentrations (MICS) of Sertaconazole and Miconazole against 107 yeasts, 47 dermatophytes and 4 fungi were determined by a two-fold dilution method. The results of these measurements are shown in the following Table I.

These results show that Sertaconazole has a somewhat different, but similar, spectrum of in vitro activity in comparison to Miconazole. Particularly, Sertaconazole is more active against Candida albicans (43.9 % higher), Candida s.p. (47.4% higher) and Scopulariopsis (75 % higher). Thus Sertaconazole is more effective than the most common commercially used product in the case of several microorganisms.

Minimum Inhibitory Concentrations (MICS) of Sertaconazole were also measured in comparison to four of the compounds described in the Martin Patent, including a compound, referred to herein as Martin Compound 1, which has the same structure as Sertaconazole, expect that the sulfur in the benzothiophene ring is replaced by an oxygen.

TABLE I

Minimum Inhibitory Concentration of Sertaconazole and Miconazole against Different Microorganisms

| Microorganism | # strains | Sertaconazole microgram/ml | Miconazole microgram/ml |
|---|---|---|---|
| Yeasts | | | |
| Candida albicans | 52 | 6.0 | 10.7 |
| Candida tropicalis | 10 | 5.6 | 5.6 |
| Torulopsis glabrata | 10 | 1.5 | 1.1 |
| Candida s.p. | 15 | 0.5 | 0.95 |
| Malasezzia furfur | 20 | 25/8 | 19/2.8 |
| Dermatophytes | | | |
| Trichophyton rubrus | 10 | 0.4 | 0.3 |
| Trichophyton mentagrophytes | 30 | 2.6 | 2.8 |
| Microsporum canis | 4 | 2.8 | 2.0 |
| Others | 3 | 2.5 | 4.0 |
| Fungi | | | |
| Scopulariopsis brevicaulis | 4 | 8.0 | 32.0 |
| Gram-positive germs | 21 | 0.97 | 0.88 |

The structure of the Martin Compound 1 is as follows:

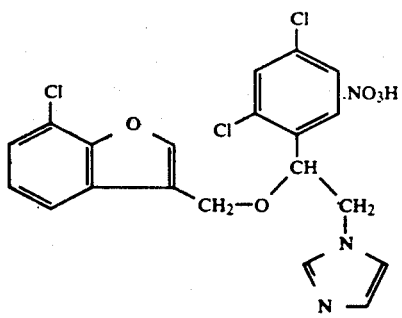

The structure of Martin Compound 2 and 3 is the same as the Martin Compound 1 except that the chlorine substituent on the benzothiophene ring is in the 6 and the 5 position, respectively, instead of the 7 position. Furthermore, the methylene group (—CH₂—) is bonded to the benzo[b]furan group in the Martin Compound 3 in the 2 position instead of the 3 position.

The structure of the Martin Compound 4 is as follows:

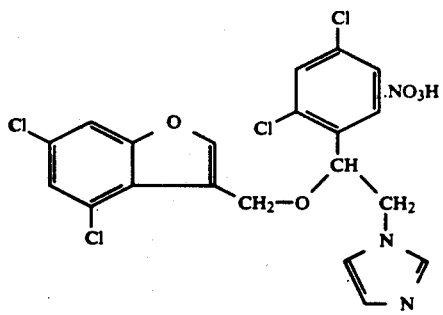

The results of comparative in vitro testing of Sertaconazole and these four Martin compounds are shown in the following Table II against 16 microorganisms.

The reading time is the time interval from the time of inoculation to the time of measurement.

Table II also shows the geometric mean of all measurements. Calculation of these geometric mean values shows that Sertaconazole is 24 % more effective than Martin Compound 1; 54 % more effective than Martin Compound 2; 16 % more effective than Martin Compound 3 and 54 % more effective than Martin Compound 4.

Thus, Sertaconazole shows an increased antimycotic activity in relation to all the Martin Compounds studied, including Martin Compound 1, in which only a benzothiophene ring sulfur is replaced by oxygen Theoretical calculations of bond angles and electron densities made by the method of Del Re, et al. Biochem.Biophys.Acta, 75, 153–182(1963) have confirmed that significant differences in chemical properties can occur, because of replacement of the oxygen atom in the benzothiophene ring with the sulfur atom. For example,

TABLE II

| Microorganism | SZ | M1 | SZ | M2 | SZ | M3 | SZ | M4 |
|---|---|---|---|---|---|---|---|---|
| C. albicans 14 | 1 | 2 $^a$ | 0.25 | 0.25 $^d$ | 0.5 | 0.5 $^d$ | 0.5 | 0.5 $^d$ |
| C. albicans 15 | 0.5 | 1 $^a$ | 0.06 | 0.06 $^d$ | 0.03 | 0.06 $^d$ | 0.03 | 0.03 $^d$ |
| C. albicans 31 | 8 | 8 $^b$ | 4 | 4 $^e$ | 4 | 4 $^e$ | 4 | 8 $^e$ |
| C. albicans 32 | 8 | 8 $^b$ | 4 | 4 $^e$ | 4 | 4 $^e$ | 4 | 8 $^e$ |
| C. albicans ATCC E-10231 | 1 | 2 $^a$ | 0.5 | 0.5 $^d$ | 0.5 | 0.5 $^d$ | 0.5 | 0.5 $^d$ |
| C. pseudotropicalis 21 | 0.03 | 0.03 $^c$ | 0.03 | 0.06 $^f$ | 0.03 | 0.03 $^f$ | 0.03 | 0.03 $^f$ |
| C. krusei 24 | 1 | 1 $^a$ | 0.25 | 0.05 $^d$ | 0.125 | 0.125 $^d$ | 0.125 | 0.5 $^d$ |
| C. krusei 24 | 0.25 | 0.25 $^b$ | 0.25 | 0.5 $^e$ | 0.25 | 0.25 $^e$ | 0.25 | 0.5 $^e$ |
| C. parapsilosis 19 | 1 | 1 $^c$ | 0.25 | 1 $^f$ | 0.25 | 0.5 $^f$ | 0.25 | 0.5 $^f$ |
| C. parapsilosis 19 | 0.5 | 0.5 $^b$ | 0.25 | 1 $^e$ | 0.5 | 1 $^e$ | 0.5 | 0.5 $^e$ |
| C. stellatoidea 36232 | 1 | 1 $^c$ | 0.25 | 0.5 $^f$ | 0.5 | 0.5 $^f$ | 0.5 | 0.5 $^f$ |
| C. stellatoidea 36232 | 0.25 | 0.5 $^a$ | 0.06 | 0.06 $^d$ | 0.06 | 0.125 $^d$ | 0.06 | 0.06 $^d$ |
| C. stellatoidea 36232 | 4 | 4 $^b$ | 1 | 1 $^e$ | 0.5 | 4 $^e$ | 0.5 | 0.5 $^e$ |
| C. guillermondii | 0.5 | 0.5 $^a$ | 0.25 | 0.5 $^d$ | 0.25 | 0.25 $^d$ | 0.25 | 0.5 $^d$ |
| C. guillermondii | 0.25 | 0.5 $^b$ | 0.25 | 0.5 $^e$ | 0.125 | 0.25 $^e$ | 0.125 | 0.5 $^e$ |
| C. tropicalis 25 | 8 | 8 $^b$ | 8 | 8 $^e$ | 4 | 8 $^e$ | 4 | 8 $^e$ |
| Geometric means | 0.876 | 1.09 | 0.366 | 0.565 | 0.336 | 0.497 | 0.336 | 0.518 |
| Increase of Sertaconazole activity | | 24% | | 54% | | 16% | | 54% |

SZ Sertaconazole
M1, M2, M3, M4 Martin compounds
$^a$ Casitone medium. Reading time 60 h
$^b$ YNB medium. Reading time 60 h
$^c$ Sabouraud medium. Reading time 60 h
$^d$ Casitone medium. Reading time 48 h
$^e$ YNB medium. Reading time 48 h
$^f$ Sabouraud medium. Reading time 48 h applicants have found by this theoretical method that the sulfur atom in Sertaconzole is significantly less negatively charged than the corresponding oxygen atom in Martin Compound 1. Furthermore, the theoretical results for the electron densities and the bond angles show that, relative to Martin Compound 1, Sertaconzaole has decreased polarity, increased lipophylicity, increased molecular volume, decreased gastrointestinal absorption and decreased toxicity.

2. In Vivo Activity

Dermal infection in albino female guinea pigs by Trichophyton mentagrophytes has been studied. Animals were distributed in three groups: a) a control group of infected untreated animals; b) a scrtaconazole group of infected and treated animals; and c) a miconazole group of infected and treated animals. Animals were depleted and a 0.4 ml suspension of the microorganism was applied on the depleted area. Treatment with each of the test drugs was made by application of 1 g of 2% cream on the depleted area on the 4th, 5th and 6th day after infection. The results are shown in the following Table III:

TABLE III

Relationship of Negative Cultures to Total Cultures (% microbiological healing) at days 18, 25 and 32 Postinfection.

| Treatment group | 18 days | 25 days | 32 days |
|---|---|---|---|
| Control | 0/24(0%) | 0/24(0%) | 5/24(21%) |
| Compound 25 | 27/48(56%) | 36/48(75%) | 40/48(84%) |
| Miconazole | 3/48(6%) | 13/48(28%) | 21/48(44%) |

Although in the in vitro experiment with *Trich. metagrophytes*, Sertaconazole was not much more active than Miconazole, in this in vivo experiment with the same microorganism Sertaconazole was surprisingly remarkably more active than Miconazole. 9 times higher on the 18th day, 2.7 times higher on the 25th day and 1.9 times higher on the 32nd day postinfection. These results show that although only small structural changes are involved large surprising changes in the rates of cure occur. These results are consistent with clinical trials.

Besides the above in vivo experiments vaginal infection by *Candida albicans* was studied in female mice. Standard methods were used. Seven days after infection sertaconazole was found to heal 75 % of the animals treated whereas miconazole only healed 12.5 %. Similar results were found in experiments where repeated dosages of active compound were used after infection. These in vivo results confirmed the surprising speed of action of Sertaconazole in comparison to the prior art compounds.

3. Toxicological Comparisons

Toxicity of Sertaconazole, Microazole and Martin's compounds 1, 2 and 3, as shown below, has been tested by standard methods. Both acute toxicity, subacute toxicity and chronic toxicity were studied Oral, intraperitoneal and subcutaneous acute toxicity of sertaconazole and miconazole have been investigated. LD50 in mouse and rat, male and female, were measured. The results are shown in Table IV following:

TABLE IV

Lethal Dose(LD50) of Sertaconazole and Miconazole through Three Different Administration Routes in Males

| Administration | Animal | Sertaconazole mg/kg | Miconazole mg/kg |
|---|---|---|---|
| Oral | mouse | >8000 | 2,560 |
| Oral | rat | >8000 | 920 |
| Intraperitoneal | mouse | >8000 | 662 |
| | rat | >8000 | 1,185 |
| Subcutaneous | mouse | >8000 | >5000 |
| | rat | >8000 | >5000 |

Table IV shows that Sertaconazole is an order of magnitude less toxic by oral and intraperitoneal routes than the prior art compound, Miconazole. Subcutaneous acute toxicity was also significantly less for Sertaconazole than Miconazole. This shows that a pharmaceutical preparation containing Sertaconazole is significantly safer to give to a person or pet suffering from an infection due to microorganisms than Miconazole (assuming equal amounts of the active ingredient are used, which is most likely since Sertaconazole is more effective than Miconazole).

In a study of prolonged subacute toxicity of Miconazole in rats, among other effects, significant hepatomegalias in females with a dosage of under 30 mg/kg p.o. and in males with a dosage of under 60 mg/kg p.o. were observed. In contrast, Sertaconazole did not show this effect, caused by hepatocite microsomal enzymes, up to a dosage of 300 mg/kg.

Chronic toxicity of Miconazole in rats resulted in a conclusion that 100 mg/kg or more dosage caused 32 % mortality, while no mortality was observed with Sertaconazole, even at dosage levels of 300 mg/kg.

Based on these finds a safe dosage for Miconazole is about 10 mg/kg, while a safe dosage for Sertaconzole is about 150 mg/kg, i.e about 15 times higher.

Similar toxicological experiments were performed for Sertaconazole, Sertaconazole nitrate, Martin Compounds 1, 2, 3 and 4. The results are shown in Table V hereinbelow. They show that Sertaconazole is unexpectedly and surprisingly less toxic than the Martin compounds.

Sertaconazole is 8 to 15 times less toxic than the Martin Compound 1, the compound of the prior art having a structure which is closest to that of Sertaconazole.

TABLE V

Toxicological Data

| Compound | $LD_{50}$ (mg/kg) (Swiss mice i.p.) | $LD_0$ (mg/kg) (Swiss mice i.p.) |
|---|---|---|
| Sertaconazole base | 8000 | 4000 |
| Sertaconazole nitrate | 8000 | 2000 |
| Martin compound 1 | 518 | 285 |
| Martin compound 2 | 640 | 235 |
| Martin compound 3 | 640 | 423 |
| Martin compound 4 | <1000[a] | Not determined |

[a]Approximate value.

Furthermore and in addition to the results shown in Table V, the mice given Martin Compounds 1 and 3 revealed evident signs of intoxication in the central nervous system, which possibly caused the death of most animals. Such signs included convulsions and Straub tail(vertical righting of the tail). These signs were not observed in mice given Sertaconazole at any dosage level. Post mortem examination showed that 80 % of the mice given Martin Compound 3 had generalized pulmonary edema and congestion to such an extent that alone could have caused their death.

Thus, Sertaconzole is unexpectedly and surprisingly safer than the closest prior art, Martin Compound 1 This implies that a higher concentration of Sertaconazole can be used safely in a pharmaceutical preparation to treat an infection in humans and pets than Martin Compound 1. However, since Sertaconazole is also more effective as an in vitro fungicidal agent, it is not necessary to use a higher concentration.

In conclusion, Sertaconazole has been shown to be unexpectedly and surprisingly better as an antimycotic agent than the closest prior art compounds.

4. Clinical Evaluation of Pharmaceutical Preparations for Treating Infections in Humans Human clinical trials were performed with Sertaconazole nitrate and Miconazole nitrate acid addition salts. Randomized double blind trials were carried out with 502 patients suffering from cutaneous mycosis as confirmed by microscopic examination and microbiological culture. 247 patients were treated with 2 % Sertaconazole cream and the remaining 255 patients were treated with 2 % Miconazole cream. All patients received scheduled treatment for 28 days and were followed up for an additional 28 days for possible relapses. The most important conclusions from these clinical trials were that Sertaconazole was 20.8% more effective than Miconazole. Also it was 100 % effective against *Trichophyton rubrum*, which produces a particularly stubborn infection, as compared to 79 % for Miconazole. Furthermore, there were 5 cases of contact dermatitis in the experiments with Miconazole, while Sertaconazole showed no such side effects.

Sertaconazole generally shows an antibacterial and antiprotozoal activity as well as an antimycotic behavior.

PHARMACEUTICAL COMPOSITIONS

For their pharmaceutical, veterinary and clinical use the compounds of the present invention or their pharmaceutically acceptable acid addition salts can be administered, in solid, semi-solid or liquid form in tablets, coated tablets, capsules, powders, suppositories, liquid solutions, suspensions, creams, lotions, ointments and the like, together with pharmaceutically acceptable non-toxic carriers or excipients normally employed. They can also be administered by the in3ectable route, rectal route and by vaginal-intrauterine route in the form of ovulum, vaginal tablets, ointment, cream, pessary, lotion, etc. They can be administered by the topical route in the form of cream, lotion, ointment, emulsion, solution shampoo, powder, gel and so forth.

Topical application is the preferred method of administration in clinical usage. Topical pharmaceutical compositions containing the compounds of the present invention exhibit antiyeast, antifungal, antiprotozoal and antibacterial activity over a wide range of concentrations, for example, from about 0.1 % to 15 % by weight of the composition, to be applied on the infected skin or mucosa, preferably in 2 to 3 daily applications.

For systematic (oral or parenteral) or rectal administration, it is expedient to administer the active ingredient in amounts between 1 and 50 mg/kg body weight for a day, preferably distributed over several applications. Exact dosage however depends on a variety of factors including of course patient's nature and condition.

Examples of pharmaceutical preparations for the treatment and control of infections due to yeast, fungi, protozoa and bacteria using compound 25 of the invention as the effective ingredient are provided in the following paragraphs

| Example 1. Topical Formulation: Dermal Cream | |
|---|---|
| Sertaconazole nitrate | 0.2-3 g |
| Benzyl alcohol | 1.00 g |
| 2-Octyldodecanol | 5.75 g |
| Liquid paraffin | 5.75 g |
| Stearic alcohol | 5.75 g |
| Cetyl alcohol | 5.75 g |
| Myristhylic alcohol | 3.00 g |
| Tween 60 | 3.50 g |
| Span 60 | 1.50 g |
| Distilled water s.q.f. | 100 g |
| Example 2. Topical Preparation: Vaginal Cream | |
| Sertaconazole nitrate | 0.2-3 g |
| Hydrogen ricinus oil | 100 mg. |
| Corn starch | 100 mg |
| Magnesium stearate | 6 mg |
| Microcrystalline cellulose s.q.f. | 1 tablet |
| Example 3. Oral Formulation: Tablets | |
| Sertaconazole nitrate | 200 mg |
| Corn starch | 80 mg |
| Lactose | 160 mg |
| Polyvinylpyrrolidone | 15 mg |
| Colloidal silicic anhydride | 1 mg |

| -continued | |
|---|---|
| Magnesium stearate | 2.5 mg |
| Microcrystalline cellulose s.q.f. | 500 mg |

Thus, the amount of the compound of formula I, or an acid addition salt thereof, administered to a patient to treat an infection caused by fungi or yeasts on a daily dosage basis amounts to from about 100 mg to about 800 mg. For topical application to treat infections of the skin 0.1 to 5 % of the compound of formula I, or an acid addition salt thereof, in the pharmaceutical carrier is preferably used.

Also the compounds of the present invention, can be used to treat crop diseases caused by fungi or yeasts. The compounds can be administered by watering, atomizing, spraying or dusting, and also in the form of a powder, cream, paste or spray at the rate of 0.1 to 15 kg per hectare.

While the invention has been illustrated and described as embodied in 1H-imidazole derivative compounds and pharmaceutical compositions containing the same for treating infections caused by fungi and yeasts in humans and pets and in crops, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of the invention.

We claim:

1. A 1H-imidazole derivative compound of formula I:

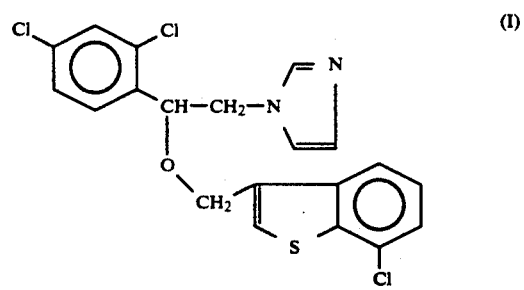

or a nontoxic addition salt thereof.

2. A pharmaceutical composition for treating infections caused by fungi or yeasts in humans and pets, comprising said compound of claim 1 in an effective amount and in combination with a pharmaceutically acceptable carrier.

3. A pharmaceutical composition according to claim 2, in dosage unit form including 100 to 800 mg of said compound.

4. A pharmaceutical composition according to claim 3 for topical application, wherein said compound is present in a concentration from 0.1 to 5 %.

5. A pharmaceutical composition composed of 0.1 to 5 % by weight of said compound of claim 1 in a pharmaceutically acceptable carrier, said compound being present in an amount of from 100 to 800 mg.

6. Method of treating infection caused by fungi or yeast in humans and pet animals, comprising administering an effective amount of the composition according to claim 2.

7. Method of claim 6, wherein said effective amount comprises a daily dose of 100 to 800 mg of said compound.

8. Method of claim 6, wherein said administering comprises oral, injection, rectal, vaginal or topical route administering.

9. Method of treating disease caused by fungi or yeast in crops, comprising applying onto or within the locus of said crops, an effective amount of a compound of claim 1 in combination with carrier means.

10. Method of claim 9, wherein said effective amount comprises 0.1 to 15 kg per hectare of soil.

11. Method of claim 9, wherein said applying comprises watering, atomizing, spraying, dusting or pasting.

12. Compound according to claim 1, wherein said acid addition salt is a nitrate salt.

13. A pharmaceutical composition for treating fungal and yeast infections in humans and pets, comprising 100 to 800 mg of a member selected from the group consisting of a 1H-imidazole derivative compound of formula I:

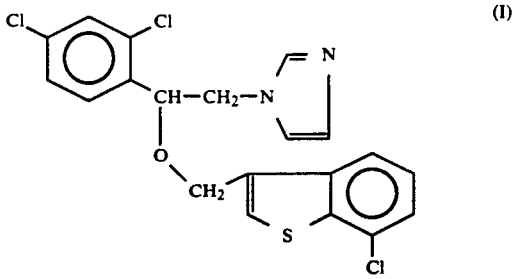

and nontoxic addition salts thereof in a pharmaceutically acceptable carrier.

14. A pharmaceutical composition according to claim 13, wherein said nontoxic addition salts include a mononitrate addition salt of said 1H-imidazole derivative compound.

* * * * *